(12) United States Patent
Kairinos

(10) Patent No.: US 7,999,145 B2
(45) Date of Patent: Aug. 16, 2011

(54) ORTHOPAEDIC PIN ISOLATOR

(76) Inventor: Nicolas Kairinos, Century (ZA)

(*) Notice: Subject to any disclaimer, the term of this patent is extended or adjusted under 35 U.S.C. 154(b) by 284 days.

(21) Appl. No.: 12/307,495

(22) PCT Filed: Jun. 28, 2007

(86) PCT No.: PCT/IB2007/052516
§ 371 (c)(1),
(2), (4) Date: May 4, 2009

(87) PCT Pub. No.: WO2008/004160
PCT Pub. Date: Jan. 10, 2008

(65) Prior Publication Data
US 2009/0318842 A1 Dec. 24, 2009

(30) Foreign Application Priority Data
Jul. 5, 2006 (ZA) .................. 2006/04593

(51) Int. Cl.
*A61F 13/00* (2006.01)

(52) U.S. Cl. .......................... 602/42; 602/52

(58) Field of Classification Search ............... 602/41–54
See application file for complete search history.

(56) References Cited

U.S. PATENT DOCUMENTS

| | | |
|---|---|---|
| 4,915,694 A | 4/1990 | Yamamoto et al. |
| 5,176,648 A | 1/1993 | Holmes et al. |
| 5,215,531 A | 6/1993 | Maxson et al. |
| 5,267,970 A | 12/1993 | Chin et al. |
| 5,354,283 A | 10/1994 | Bark et al. |

FOREIGN PATENT DOCUMENTS

| | | |
|---|---|---|
| DE | 90 17 289 | 4/1992 |
| DE | 19837762 | 1/2000 |
| EP | 0659390 | 6/1995 |
| WO | WO-93/07928 | 4/1993 |
| WO | WO-99/65413 | 12/1999 |

*Primary Examiner* — Michael A. Brown
(74) *Attorney, Agent, or Firm* — Connolly Bove Lodge & Hutz LLP

(57) ABSTRACT

A wound management accessory (10) and a method of dressing a wound (28,30) in the vicinity of an external orthopaedic fixator pin (24) are provided. The accessory (10) has a resilient body with a sleeve (12) defining an inner bore (18) that is shaped and dimensioned to fit around the circumference of the fixator pin (24) with an interference fit. The body also defines a flange (14) extending radially from the bore. The method comprises applying the accessory (10) to the pin (24) by passing the pin through the bore (18), covering the wound (28,30) at least in part with an occlusive adherent film (34), attaching at least the flange (14) of the accessory to the film in a generally sealing manner and applying a negative pressure to the wound beneath the film.

29 Claims, 5 Drawing Sheets

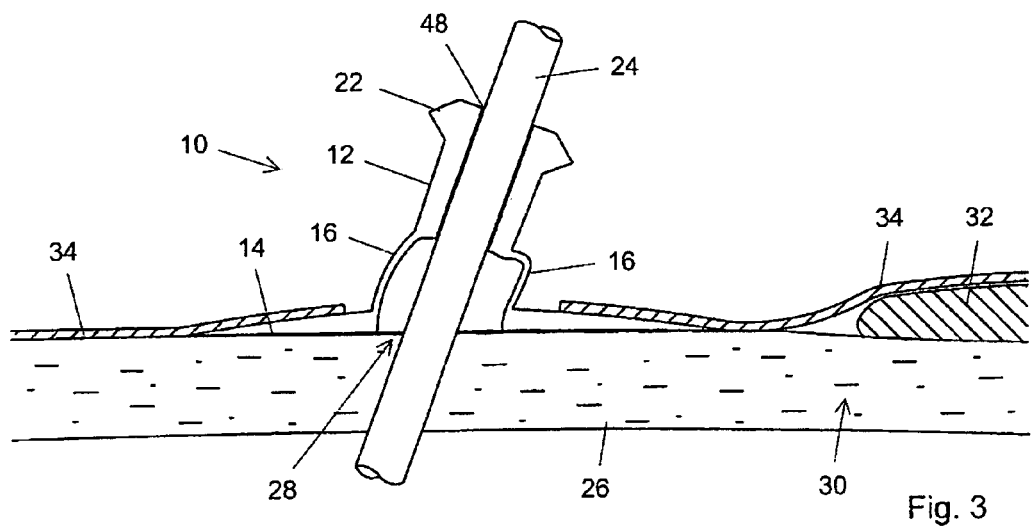
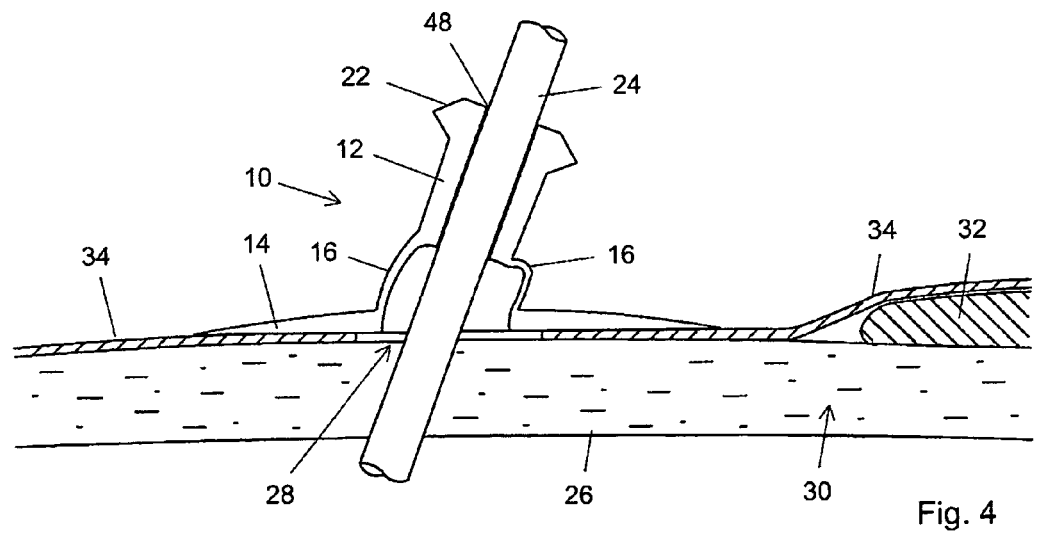

ORTHOPAEDIC PIN ISOLATOR

CROSS REFERENCE TO RELATED APPLICATIONS

This application is a national phase of PCT/IB2007/052516, filed on Jun. 28, 2007, which claims priority to ZA 2006/04593, filed on Jul. 5, 2006, the entire contents of which are incorporated herein by reference in their entireties.

FIELD OF THE INVENTION

This invention relates to wound management, especially in the fields of orthopaedic and plastic surgery. In particular, the invention relates to a wound management accessory and a method of dressing a wound.

BACKGROUND TO THE INVENTION

Orthopaedic external fixator devices are used for facilitating bone union in fractured limbs, particularly when open wounds are present. Pins, which are driven into the bone on either side of the fracture protrude through the skin and are attached to a frame outside of the body. The wounds commonly found overlying the fracture are often treated with negative pressure wound therapy (vacuum dressings). These dressings comprise a spongy material placed in the wound, covered by an occlusive adherent film dressing. Tubing placed in contact with the sponge, beneath and sealed off by the adherent film, is attached to a source of suction and suction via the tubing causes a negative pressure within the sponge. This type of negative pressure wound therapy has revolutionised the management of these open wounds as it promotes wound healing, decreases swelling and draws away excess wound exudate and associated bacteria.

Placing of the adherent film dressing over the sponge is difficult in the presence of the pins and creating an airtight seal around the base of these pins by attempting to stick the film to them often creates leaks, allowing ingress of air and thus inhibiting vacuum formation. This is due to the fact that creases in the adherent film often cause leaks by acting as micro channels through which ambient air can be drawn in underneath the film. Attempting to apply the adherent film around these pins without getting creases is near impossible.

A number of techniques have being devised in attempts to address this common problem. One method is to seal leaks with a hydrocolloid paste applied to locations of leaks. This can however be time-consuming as the doctor has to search for these leaks. Another method is to create a "mesentery". This involves applying half of the film to the skin or foam and then running the other half up the shaft of the pin. Another film is then applied on the opposite side of the pin, to the skin and pin, mirroring the first film, in so doing sandwiching the pin between the two adherent sides of the films and thereby creating a seal around the pin. This technique holds the disadvantages that it is very time-consuming, particularly as there are multiple pins to which such mesenteries need to be applied and the overlying structures of the external fixators restrict access to the wounds and thus makes the application of these mesenteries very difficult. This technique also increases the quantities of adherent film required for these types of dressings. This technique is further not infallible and may also leak if there are creases in the film or if two pins are place close to each another, causing a tendency of the two adherent films to separate from each other between the two pins, since attempts to avoid the formation of creases tend to keep the films in planar conditions and not to allow them to penetrate between the pins. Often the threaded part of the screw protrudes a fair distance outside the flesh entry site and it can be difficult to apply the adherent film to this threaded part in a sealing manner, with the result that leaks at these sites are more likely.

In order to increase the adhesion of the film to the skin and the base of the pin and thus to create a good seal and reduce the likelihood of a leak, the use of any materials that could reduce adhesion is typically avoided. However, this also rules out the use of antibacterial dressings and ointments around the base of a pin prior to applying the film and the potential risk of infection at the point of entry of the pin in the skin is greatly increased. This complication is relatively common even in the presence of antibacterial agents, with literature quoting figures between 10 and 50% depending on the definition of "infection". The presence of the adherent film around the pin sites creates a moist environment, ideal for bacterial proliferation. This, combined with the fact that no antibacterial dressings are used, implies that pin site infection rates in these dressings are likely to be even higher. Depending on the severity of the infection, these patients may require more frequent hospital attendances and dressing changes, antibiotics or even removal of the pins prior to bone union taking place. Should the infection spread to the bone, the resulting osteomyelitis could further complicate the patient's recovery.

Devices have been developed which help to secure antibacterial dressings around the pin entry site, but these are not compatible with vacuum dressings as they make the possibility of creating a seal around the pins even more difficult. Other products have been described which envelope the pins in a sheath-like manner and are impregnated with antibacterial substances. However, these products also do not facilitate the possibility of creating a seal around the pins when used with vacuum dressings.

The present invention seeks to provide improved application of negative pressure wound therapy dressings in the presence of orthopaedic pins, which inhibits the disadvantages of existing techniques and apparatus as described above. In particular, the invention seeks to provide reliable and convenient sealing of the dressings and to allow for the use of antibacterial dressings around the bases of the pins.

BRIEF DESCRIPTION OF THE INVENTION

According to one aspect of the present invention there is provided a wound management accessory comprising a body of resilient material, said body defining an inner bore that is shaped and dimensioned to fit around the circumference of an orthopaedic fixator pin with an interference fit, wherein said body defines a flange extending radially from the bore.

The body may include an annular sleeve with the bore defined inside the sleeve and at least one circumferential rib may be defined on the inner circumference of the bore.

The body may include a flexible connection between one end of the sleeve and the inner circumference of the flange and the body may have a circumferential wall in the flexible connection, with a thickness that is smaller than the wall thickness of the annular sleeve.

The accessory may include at least one grip formation such as a radial rib protruding from the outer circumference of the sleeve and which is spaced from the flange.

The bore may widen in the vicinity of the flange.

The body may be made of an elastomeric material such as silicone and/or the flange may include an adhesive layer.

The flange may taper in thickness towards its periphery and at least one radial groove may be defined in the underside of the flange.

The body may define at least one recess in the vicinity of the inner circumference of the flange, in which an antimicrobial substance may be receivable.

The body may be split along a slit extending the length of the bore and extending radially outwardly to allow the accessory to be slid onto a fixator pin by passing the pin through the slit, the resilience of the body tending to keep the slit closed. In such a case, the accessory may define at least one aperture extending through the flange.

According to another aspect of the present invention there is provided a method of dressing a wound in the vicinity of an external orthopaedic fixator pin, including, but not limited to the pin site wound, said method comprising:

covering the wound with an occlusive adherent film; and applying a negative pressure to the wound, beneath the film;

said method including applying an accessory as claimed in any one of claims 1 to 15 to the pin and attaching at least the flange of the accessory to the film in a generally sealing manner.

The accessory may be applied to the pin before the wound is covered with the film, so that the film is applied over the flange of the accessory or instead, the accessory may be applied to the pin after the wound is covered with the film, so that the flange of the accessory is applied over the film.

An antimicrobial substance may be applied to the pin site wound before applying the film and the antimicrobial substance may be applied to the underside of the accessory.

BRIEF DESCRIPTION OF THE DRAWINGS

For a better understanding of the present invention, and to show how the same may be carried into effect, reference will now be made, by way of non-limiting example, to the accompanying drawings in which:

FIG. 3 is a sectional view of the accessory of FIG. 1 in use in a first embodiment of a method in accordance with the present invention;

FIG. 4 is a sectional view of the accessory of FIG. 1 in use in a second embodiment of a method in accordance with the present invention;

DETAILED DESCRIPTION OF THE DRAWINGS

Figure 1:
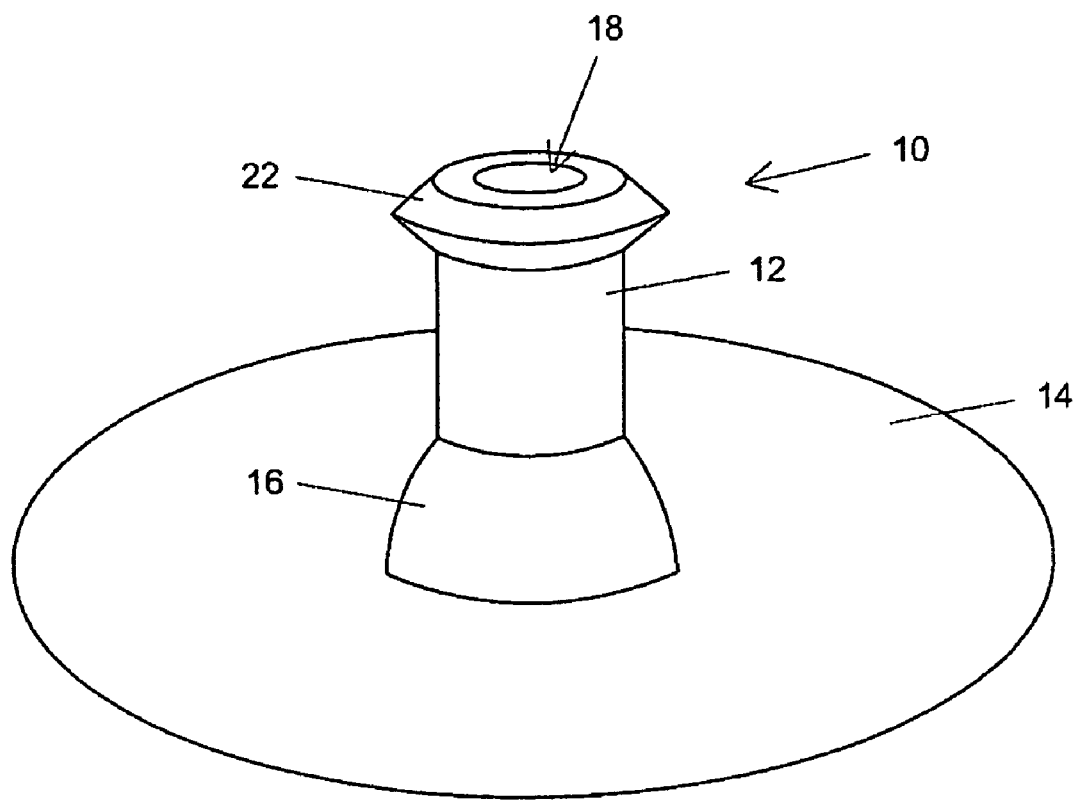
FIG. 1 is a three-dimensional view of a first embodiment of a wound management accessory in accordance with the present invention.

Referring to the drawings, a wound management accessory in the form of an orthopaedic pin isolator is generally indicated by reference numeral 10. The same reference numerals are used in all the drawings for features that are common to different embodiments of the present invention.

Figure 2:
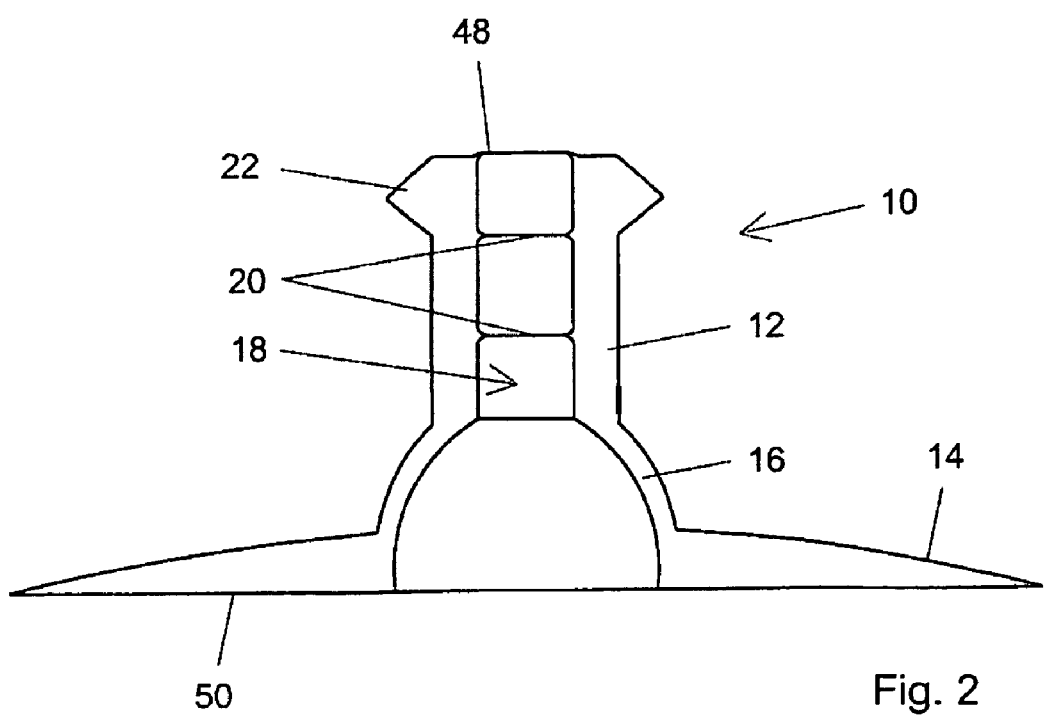
FIG. 2 is a sectional side view of the accessory of FIG. 1.

Referring firstly to FIGS. 1 and 2, the isolator 10 comprises a body of resilient material, e.g. rubber or preferably silicone. The body defines an annular sleeve 12 and a disc-shaped radial flange 14 that is connected to the one end of the sleeve by a flexible connection 16. A central bore 18 extends centrally in an axial direction through the accessory 10 and widens inside the flexible connection 16, adjacent the flange 14. The wall thickness of the sleeve 12 is significantly more than that of the flexible connection 16 and the thickness of the flange 14 tapers towards its outer circumference. Two circumferential ribs 20 are defined on the inside the bore 18 and a grip formation 22 in the form of a circumferential rib extends radially outwardly from the top of the sleeve 12. A third rib 48 protrudes inwardly from the inner circumference of the upper opening of the bore 18.

Referring to FIG. 3, the isolator of FIGS. 1 and 2 is shown in use in a wound associated with an external orthopaedic fixator pin 24. The pin 24 is shown penetrating the skin 26 of a patient at an oblique angle, for illustrative purposes, but could instead be oriented generally perpendicular to the skin. The wound or site 28 where the pin 24 penetrates the skin 26, as well as an adjacent wound (the location of which is indicated generally by reference numeral 30) need to be covered in a negative pressure (i.e. a "vacuum") dressing.

Once the pin 24 has been installed, i.e. after it has been drilled into a bone of the patient, but before the overlying frame is connected to the pin, the isolator 10 is slid onto the pin, with the sleeve 12 gripping the pin in a tight, sealing manner owing to an interference fit between the bore 18 and the pin's circumference. The bore 18 is shaped and dimensioned to ensure such a seal and the seal is enhanced by the ribs 20 that are pressed tightly against the pin 24 and that are particularly useful to compensate for possible loss of the interference fit between the sleeve and the pin when the sleeve is strained, e.g. warped. Even in the event that a screw thread is defined on the circumference of the pin 24 where it contacts the bore 18, a good seal between the bore and the pin can be achieved owing to the flexibility of the soft silicon, the interference fit and the ribs 20, 48 protruding into the screw thread.

Further, the sliding movement of the isolator 10 along the pin 24 causes the rib 48 to "drag" along the pin and to extend slightly upwardly along the pin when in position. With this orientation, the rib 48 is particularly effective in preventing the passage of gas or liquid downwardly into the bore (if there were a gap between the bore and the pin 24), since any pressure differential with higher pressure above the rib 48 will press it downwardly and thus tighter against the pin.

The isolator 10 is slid along the pin until its flange 14 abuts the skin 26 right around the site 28 at the base of the pin 24. In order for proper sealing contact to be achieved between the flange 14 and the skin 26, the flange needs to flex to extend at an oblique angle relative to the pin, flush with the skin. This is achieved by flexion of the relatively thin walls of the connection 16 which buckles or "concertinas", while the shapes of the sleeve 12 and flange 14 remain substantially unchanged. Further, the isolator 10 compensates for the fact that the site 28 is not necessarily round and/or that the site 28 may be off centre relative to the isolator in instances where the pin 24 extends at an oblique angle, by way of the widened bore inside the flexible connection 16. The widened bore also allows space for the flexion of the wall of the connection 16.

Once the isolator 10 has been positioned with the sleeve 12 sealing against the pin 24 and with the flange 14 in sealing abutment with the skin 26, a negative pressure dressing is applied using a porous structure such as foam 32 placed on the wound 30, connected to a vacuum source and covering the foam with an occlusive adherent film 34.

Figure 9:
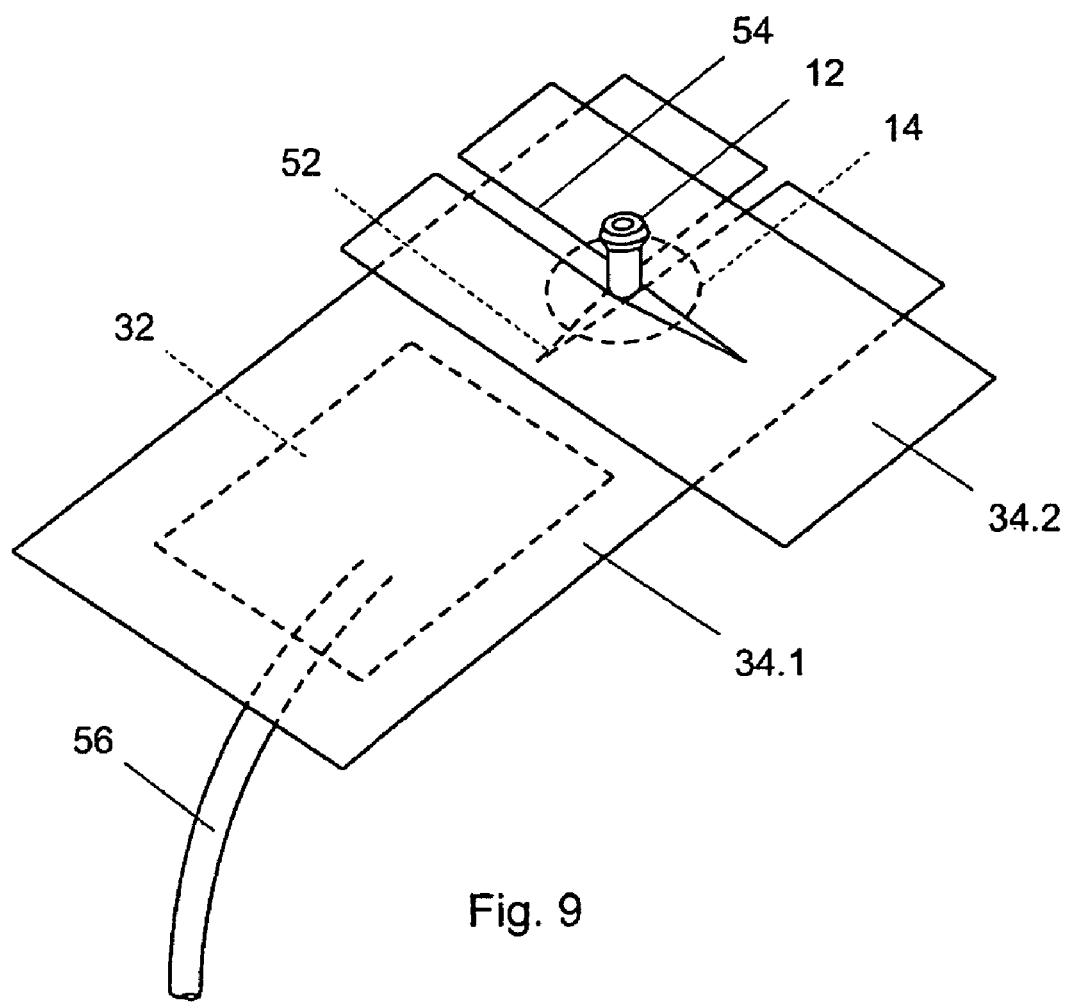
FIG. 9 is a three dimensional view of the accessory and some ancillary apparatus of FIG. 3.

The parts of the vacuum dressing, particularly the lay-up of the film 34 are illustrated more clearly in FIG. 9, from which the pin 24 has been omitted and in which the sleeve 12 is shown in a normal, perpendicular orientation—for simplicity. In embodiments of the invention where the flange 14 extends underneath the film (i.e. as illustrated in FIG. 3), the film 34 can typically be applied making a slit 52 in a first sheet of film 34.1 and laying the sheet 34.1 up with the sleeve 12 passing through the slit. In order to ensure a seal around the entire circumference of the flange 14, a second sheet of film 34.2 is slit and is laid over the first sheet 34.1 with the sleeve 12 passing through the slit, with the slits 54 and 52 orientated generally perpendicular to each other. The same technique can be used to apply the film 34 in two sheets with slits 52 and 54 at different orientations in embodiments of the invention where the flange 14 extends above the film and adheres to the top of the film (i.e. as illustrated in FIG. 4), preferably after peeling of the backing 50 described below. It is to be appreciated that the geometries of wounds and the positions of pins 24 vary drastically, with the result that different methods of applying the film 34 have to be devised for different cases.

Referring to FIGS. 3 and 9, suction is applied to the dressing by the vacuum source (via tube 56 shown in FIG. 9) which draws air from the foam 32 and the foam collapses due to atmospheric pressure acting on the outside of the dressing. The seal of the isolator 10 against the pin 24 obviates the need for the film 34 to be sealed against the pin and thus fulfils the function of a mesentery as used in existing practice. However, the configuration of the flange 14 that extends quite flatly along the skin 26 surface with very thin circumferential edges, allows for the film 34 to be applied to the surface of the skin with ease and with minimal risk that the dressing would leak as a result of film creases, inadequate sealing between the film and the flange, or the like.

The dressing may need to be changed from time to time and/or the site 28 may need to be inspected and in order to achieve this, the isolator can easily be slid up the pin 24 by gripping the grip formation 22. During this action, the ribs 20 scrape off unwanted matter from the pin 24 and thus limit the risk that some of this matter will be advanced with the isolator when it is slid downwardly into position when the dressing is re-applied.

Referring to FIG. 4, the isolator of FIGS. 1 and 2 is shown in use in a method similar to that shown in FIG. 3, except that the isolator is slid into position after the dressing has been applied, with the result that the flange 14 extends over the film 34 instead of beneath it. In order to ensure an adequate seal between the flange 14 and the film 34, the underside of the flange is treated with an adhesive.

The same adhesive on the underside of the flange 14 as described with reference to FIG. 4 can also be of assistance in providing a good seal between the flange 14 and the skin 26 in the method shown in FIG. 3. Movement of soft tissues around the pin 24 has often been implicated as an important factor in the development of pin site infection. The adherence of the flange 14 to the skin 26 could minimise this movement and therefore further decrease the risk of infection.

The isolator 10 with the adhesive flange 14 preferably comes with a "peel off" backing 50 (as shown in FIG. 2) that covers the adhesive layer until it is removed to expose the layer. If adhesiveness is not required, the backing can be kept on the flange 14 and the isolator 10 can be used as a non-adhesive pin isolator. The adhesive properties of the underside of the flange 14 may be imparted by the properties of "softer" silicone compounds which are inherently adhesive and which thus allow the flange 14 to retain its adhesiveness, despite repeated dressing changes. If the isolator 10 is made of silicone, the film 34 will easily stick to it in a sealing manner, but will be easy to peel off to allow for dressing changes using the same pin isolators 10.

Figure 5:
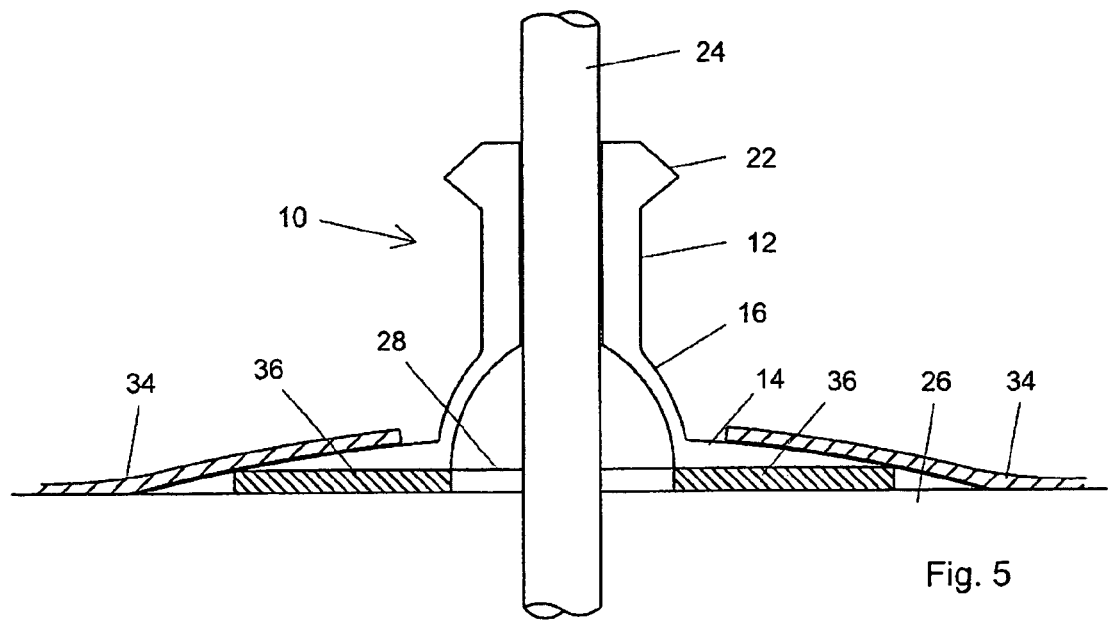
FIG. 5 is a sectional view of the accessory of FIG. 1 in use in a third embodiment of a method in accordance with the present invention.
Figure 6:
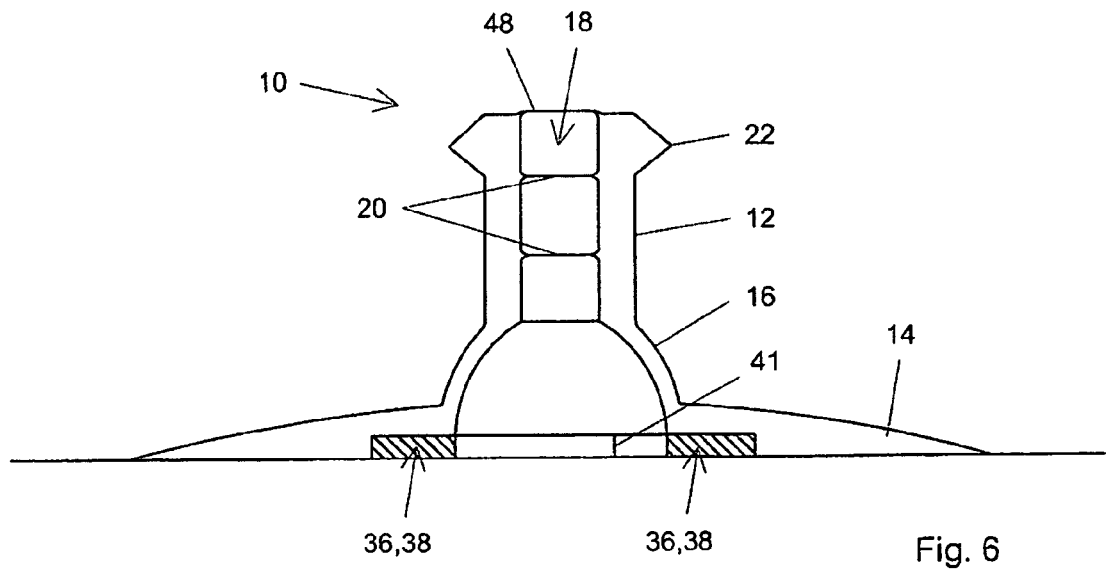
FIG. 6 is a sectional view of a second embodiment of a wound management accessory in accordance with the present invention.

Referring to FIGS. 5 and 6, the primary purpose of the isolator 10 is to render an airtight seal around the base of the pin 24, but a secondary purpose is the prevention of pin site infection. Antimicrobial dressings and/or ointment can be placed underneath the dressing and/or the isolator 10, but in preferred embodiments, an antimicrobial dressing 36 is attached to the underside of the flange 14 as shown in FIG. 5 or is received in a recess 38 defined in the underside of the flange as shown in FIG. 6. The antimicrobial dressing 38 can be impregnated or coated with antibacterial substances (e.g. silver) in order to create an environment which inhibits bacterial growth. In another embodiment, the underside of the flange 14 can itself be treated with an antibacterial substance.

Referring to FIG. 6, the antimicrobial dressing in the recess 38 is in the form of a disc 36 that has a central hole through which the pin 24 can pass and a slit 41 extending radially to the periphery of the disc, so that the disc may be removed and a fresh one applied when necessary.

Figure 7:
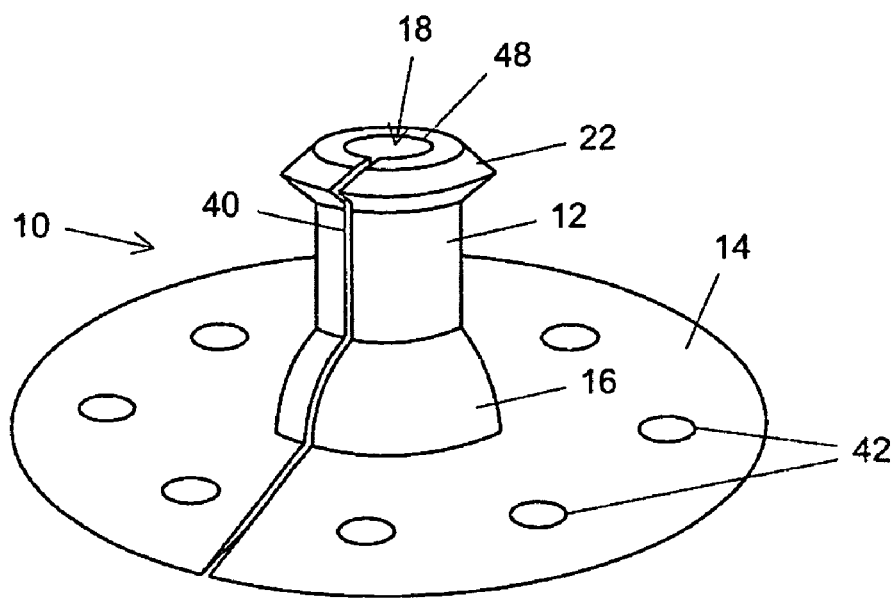
FIG. 7 is a three dimensional view of a third embodiment of a wound management accessory in accordance with the present invention.

Referring to FIG. 7, if not used for its pin sealing properties, i.e. in the absence of a vacuum dressing, the isolator 10 can be slit from top to bottom on one side, from the centre of the core to the periphery of the flange. Such a slit 40 allows the isolator to be applied to a pin 24 even after the entire external fixator is already in place. The resilient elastic properties of the isolator 10 allow it to return to its original shape after it has been applied to the pin. The potential loss of the airtight seal due to the slit 40 is irrelevant in this case because a vacuum is not required and the isolator can still be used to secure an antimicrobial dressing or ointment, or simply create an antimicrobial environment by having an antimicrobial coated flange 14. It can also be used for its skin-to-pin interface immobilising capabilities if used with an adhesive flange 14. Further, in the absence of a vacuum dressing, the flange 14 can define apertures 42 to allow venting, which can be particularly useful if the pin site 28 is oozing excessively.

Figure 8:
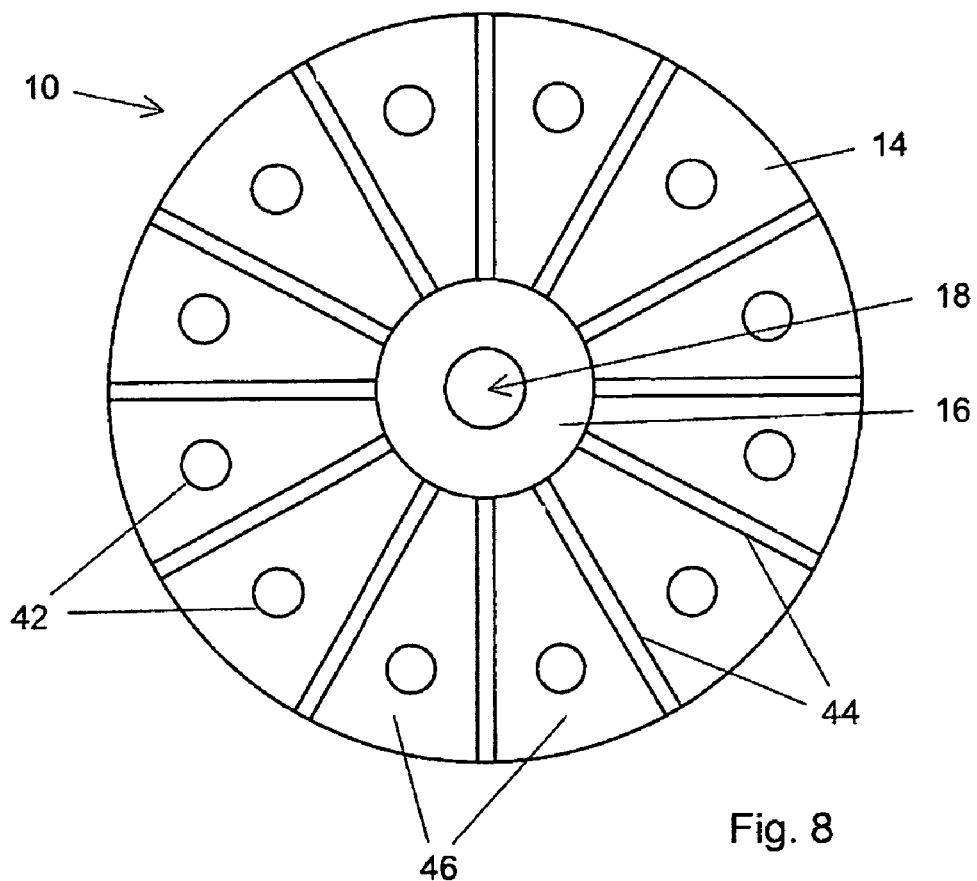
FIG. 8 is a bottom view of a fourth embodiment of a wound management accessory in accordance with the present invention.

Referring to FIG. 8, in another embodiment, the undersurface of the flange 14 defines a number of grooves 42 or micro-corrugations radiating from the centre toward the periphery, which aids in wicking excessive fluid away from the pin site 28. In order for this wicking-type flange 14 to adhere to the skin 26, the undersurface of the flange also defines broader flat surfaces 46 between the grooves 44, on which adhesive can be applied for such adhesion. The flange 14 can also define vent apertures 42 as mentioned above.

The isolator 10 can be made of a transparent or translucent material, which could give a visual indication of complications such as bleeding or sepsis at the site 28, while the isolator is in position.

The invention claimed is:
1. A wound management accessory comprising a body of resilient material, said body including:
 an annular sleeve defining an inner bore inside the sleeve that is shaped and dimensioned to fit around the circumference of an orthopaedic fixator pin with an interference fit, said body extending continuously around the bore and at least one circumferential rib being defined on the inner circumference of the bore;
 a flange extending radially from the bore; and
 at least one grip formation protruding from the outer circumference of the sleeve, spaced from the flange;

wherein said body defines at least one recess in the vicinity of the inner circumference of the flange and said recess contains an anti-microbial substance.

2. An accessory as claimed in claim 1, wherein the body includes a flexible connection between one end of the sleeve and the inner circumference of the flange.

3. An accessory as claimed in claim 2, wherein the body has a circumferential wall in the flexible connection with a thickness that is smaller than the wall thickness of the annular sleeve.

4. An accessory as claimed in claim 1, wherein the bore widens in the vicinity of the flange.

5. An accessory as claimed in claim 1, wherein the body is made of an elastomeric material.

6. An accessory as claimed in claim 5, wherein the body is made of silicone.

7. An accessory as claimed in claim 1, wherein said flange includes an adhesive layer.

8. An accessory as claimed in claim 1, wherein the flange tapers in thickness towards its periphery.

9. An accessory as claimed in claim 1, wherein said body defines at least one radial groove in the underside of the flange.

10. A method of dressing a wound in the vicinity of an external orthopaedic fixator pin, said method comprising:
    covering the wound at least in part with an occlusive adherent film
    applying a negative pressure to the wound, beneath the film; and
    applying an accessory according to claim 1 to the pin and attaching at least the flange of the accessory to the film in a generally sealing manner.

11. A method as claimed in claim 10, wherein the accessory is applied to the pin before the wound is covered with the film, so that the film is applied over the flange of the accessory.

12. A method as claimed in claim 10, wherein the accessory is applied to the pin after the wound is covered with the film, so that the flange of the accessory is applied over the film.

13. A method as claimed in claim 10, which includes applying an antimicrobial substance to the wound before applying the film.

14. A method as claimed in claim 13, in which the antimicrobial substance is applied to the underside of the accessory.

15. A wound management accessory comprising a body of resilient material, said body including:
    an annular sleeve defining an inner bore inside the sleeve that is shaped and dimensioned to fit around the circumference of an orthopaedic fixator pin with an interference fit, said body extending continuously around the bore and at least one circumferential rib being defined on the inner circumference of the bore;
    a flange extending radially from the bore; and
    at least one grip formation protruding from the outer circumference of the sleeve, spaced from the flange;
    wherein said body defines at least one radial groove in the underside of the flange.

16. An accessory as claimed in claim 15, wherein the body includes a flexible connection between one end of the sleeve and the inner circumference of the flange.

17. An accessory as claimed in claim 16, wherein the body has a circumferential wall in the flexible connection with a thickness that is smaller than the wall thickness of the annular sleeve.

18. An accessory as claimed in claim 15, wherein the bore widens in the vicinity of the flange.

19. An accessory as claimed in claim 15, wherein the body is made of an elastomeric material.

20. An accessory as claimed in claim 19, wherein the body is made of silicone.

21. An accessory as claimed in claim 15, wherein said flange includes an adhesive layer.

22. An accessory as claimed in claim 15, wherein the flange tapers in thickness towards its periphery.

23. An accessory as claimed in claim 15, wherein said body defines at least one recess in the vicinity of the inner circumference of the flange, in which an antimicrobial substance is receivable.

24. An accessory as claimed in claim 23, which includes an anti-microbial substance, in the recess.

25. A method of dressing a wound in the vicinity of an external orthopaedic fixator pin, said method comprising:
    covering the wound at least in part with an occlusive adherent film
    applying a negative pressure to the wound, beneath the film; and
    applying an accessory according to claim 15 to the pin and attaching at least the flange of the accessory to the film in a generally sealing manner.

26. A method as claimed in claim 25, wherein the accessory is applied to the pin before the wound is covered with the film, so that the film is applied over the flange of the accessory.

27. A method as claimed in claim 25, wherein the accessory is applied to the pin after the wound is covered with the film, so that the flange of the accessory is applied over the film.

28. A method as claimed in claim 25, which includes applying an antimicrobial substance to the wound before applying the film.

29. A method as claimed in claim 28, in which the antimicrobial substance is applied to the underside of the accessory.

* * * * *